United States Patent [19]

Nissen

[11] Patent Number: 4,992,470

[45] Date of Patent: Feb. 12, 1991

[54] METHOD OF ENHANCING IMMUNE RESPONSE OF MAMMALS

[75] Inventor: Steven L. Nissen, Ames, Iowa

[73] Assignee: Iowa State University Research Foundation, Inc., Ames, Iowa

[21] Appl. No.: 477,240

[22] Filed: Feb. 8, 1990

[51] Int. Cl.$^5$ .............................................. A61K 31/185
[52] U.S. Cl. ..................................... 514/578; 514/885
[58] Field of Search ................................. 514/578, 885

[56] References Cited

PUBLICATIONS

Chem. Abst. 108:74242a (1988), Nissen.
Chem. Abst. 104:49689m (1986), Meerson et al.
Chem. Abst., 106:78426v (1987), Kryzhanovskii.
Kuhlman, Roth and Nissen, Abstract 236, FASEB Journal, vol. 3, No. 3, dated Feb. 9, 1989 (published Feb. 10, 1989—see attached letter.)

Primary Examiner—Douglas W. Robinson
Assistant Examiner—Zohreh A. Fay

[57] ABSTRACT

β-methyl-β-butyrate (HMB) has been found to be markedly more effective for activating the immune function of T lymphocytes of mammals than α-ketoisocaproate (KIC). For activation of the T lymphocytes, β-methylbutyric acid or an edible water-soluble salt thereof is administered to the mammal by a route through which the HMB enters the blood of the mammal. The amount administered is sufficient for effective enhancement of the blastogenesis of their T lymphocytes. The method is adapted for use with domestic mammals, including particularly cattle, sheep, and swine. HMB can also be used with humans as an immune system stimulant.

5 Claims, No Drawings

METHOD OF ENHANCING IMMUNE RESPONSE OF MAMMALS

FIELD OF INVENTION

The field of the invention is methods of enhancing the immune response of mammals, and more particularly, the immune function of T lymphocytes.

BACKGROUND OF INVENTION

The keto analog of L-leucine (a dietarily essential amino acid) is α-keto-isocaproic acid, which is usually referred to as ketoisocaproate (KIC), or sometimes also as ketoleucine. In the accepted description of leucine metabolism, leucine is first transaminated to its ketoacid, α-ketoisocaproate (KIC). KIC then enters the mitochondria and is decarboxylated to isovalarylCoA by the branched chain ketoacid dehydrogenase. [See Krebs, et al., *Adv. Enz. Reg.* 15:375–394 (1976); and Paxton, et al., *J. Biol. Chem.* 257:14433–14439 (1982).] An alternate minor pathway has been described in the rat and human liver [Sabourn, et al., *Fed. Proc.* 38:283 (1979)]. This alternate oxidative pathway occurs in the cytosol and involves oxidation of KIC to β-hydroxy-β-methyl butyrate (HMB) by the enzyme KIC-oxygenase [Sabourn, et al., *Arch. Biochem. Biophys.* 206:132–144 (1981)].

The administration of keto analogs of amino acids has been proposed for treatment of certain disease conditions in humans, such as uremia. [See, for example, Walser, et al., *J. Clin. Inv.*, 52:678–690 (1973).] For nutritional purposes, it is known that KIC is an inefficient substitute for leucine. Rat studies have shown that the feeding of KIC as a replacement for leucine requires the feeding of from two to three times as much KIC as the nutritionally required amount of leucine: Chawla, et al., *J. Nutr.*, 105:798–803 (1975); and Boebel, et al., *J. Nutr.*, 112: 1929–1939 (1982); and Chow, et al., *J. Nutr.*, 104: 1208–1214 (1974).

It has been proposed to feed small amounts of KIC in conjunction with animal diets containing sufficient leucine for the purpose of improving the growth metabolism of the animals. By using milligram amounts of KIC, some increases in the rates of weight gain and/or feed efficiencies have been obtained. [See, for example, U.S. Pat. Nos. 4,760,090 and 4,883,817.] With mature sheep being fed for wool production, by feeding KIC the amount of wool produced may also be increased (U.S. Pat. No. 4,760,090). When lactating domestic animals, such as dairy cattle, are fed small amounts of KIC, the quantity of milk produced may be increased (U.S. Pat. No. 4,758,593). Egg production by laying chickens can also sometimes be increased (U.S. Pat. No. 4,760,531). Other effects of feeding KIC have been observed, including cholesterol reduction in meat, milk and eggs (U.S. Pat. Nos. 4,760,090 and 4,760,531). U.S. Pat. No. 4,835,185 describes the use of KIC as an immunomodulator for improving commercial performance of domestic animals. Specifically, the feeding of KIC is disclosed as a means for activating the blastogenesis function of the immune systems of the domestic animals, the KIC being administered in an amount enhancing blastogenesis of their T lymphocytes. It also disclosed that the administration of KIC will usually decrease plasma cortisol levels.

SUMMARY OF INVENTION

β-methyl-β-butyrate (HMB) has been found to be markedly more effective for activating the immune function of T lymphocytes of mammals than α-ketoisocaproate (KIC). For activation of the T lymphocytes, β-methyl-butyric acid or an edible water-soluble salt thereof is administered to the mammal by a route through which the HMB enters the blood of the mammal. The amount administered is sufficient for effective enhancement of the blastogenesis of their T lymphocytes. The method is adapted for use with domestic mammals, including particularly cattle, sheep, and swine. HMB can also be used with humans as an immune system stimulant.

DETAILED DESCRIPTION

The compound used for practicing the present invention is β-hydroxy-β-methyl butyric acid or an edible butyrate salt thereof. The free acid compound is also called β-hydroxy-isovalaryic acid. It has the following structure:

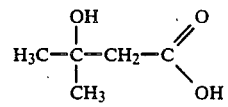

This compound in both free acid and salt form is referred to herein generically as "HMB". The acid form is designated HMB acid, and the specific salt form, such as the calcium or sodium salts, as Ca-HMB or Na-HMB. HMB has no isomers and accordingly does not exist in L or D forms. For the purpose of the present invention, it is preferred to employ HMB in the form of an edible salt rather than as the free acid. Preferably the salt form is water-soluble or becomes water-soluble in the stomach or intestines. A preferred salt is the calcium salt (Ca-HMB). Sodium (Na-HMB) can also be used but Na-HMB is more hydroscopic than Ca-HMB. Other nontoxic salts can be used such as other alkali metal or alkaline earth metal salts. For mixing with feed ingredients, it is preferred that the salt form be dry, non-sticky, and finely-divided for blending with the feed materials. Ca-HMB is particularly desirable for these reasons.

HMB is not known to be commercially available. However, procedures are known for synthesizing this compound from commercially available starting materials. For example, HMB can be synthesized by oxidation of diacetone alcohol (4-hydroxy-4-methyl-2-pentanone). One suitable procedure is described by Coffman, et al., *J. Am. Chem. Soc.*, 80:2882–2887, at 2885 (1958). As there described, β-hydroxy-isovalaryic acid (HMB) is synthesized by an alkaline sodium hypochlorite oxidation of diacetone alcohol. The product is recovered in free acid form, which can be converted to the desired salt. For example, HMB can be prepared as its calcium salt (Ca-HMB) by a similar procedure to that of Coffman, et al. in which the HMB acid obtained is neutralized with calcium hydroxide, and recovered by crystallization from an aqueous ethanol solution. For example, a 95% ethanol solution can be used with the Ca-HMB at about a 10% concentration. Such a procedure is illustrated in more detail in the following examples.

To assure administration at a desired level to domestic animals, it is preferred to mix the dry HMB salt with dry feed ingredients to a predetermined concentration. The HMB salt can be incorporated by dry blending using standard mixing equipment. The HMB should be substantially uniformly distributed throughout the feed. After mixing, if desired, the feed material may be further processed, such as by conversion to pellets. Most feed compositions for domestic animals are composed of mixtures of feed ingredients. These feed compositions contain protein-providing ingredients as principal components. These feed ingredients usually provide at least 10% protein by weight on a total dry matter basis, and may contain as much as 24% or more by weight. Such mixed feed compositions may comprise complete feeds or feed concentrates.

The method of this invention is believed to be suitable for use with all mammals, including particularly large domestic mammals such as cattle, sheep, swine, goats, and horses. It can also be used with mammals is adapted for use with zoo mammals. It is believed that a particularly important use of the method is for improving the immune system of humans.

When HMB is combined with the feed material as a uniform mixture, and the feed composition provides the major food source for the diet, the amount of HMB may be specified in relation to the feed composition. For example, the admixed total ration feed compositions may contain from 0.001 to 0.5 wt % HMB (Ca-HMB and dry feed basis). On the same basis, a presently preferred range is from about 0.01 to 0.1 wt. % HMB. Such complete feed compositions will usually contain at least 10% protein and may contain up to 24% protein (N x 6.25). For example, beneficial effects on the immune system, especially enhanced blastogenesis of T lymphocytes, can be obtained in preferred embodiments by incorporating from about 0.02 to 0.04 wt. % (dry basis) of Ca-HMB or molar equivalent amount of another edible nontoxic water-soluble salt of HMB.

The foregoing feed composition levels of HMB relate primarily to feeds which are formulated to comprise substantially the total ration of the animal. Where feed supplements or feed concentrates are employed as the vehicle for administering the HMB, greater concentrations may be required. The concentrations can be similarly related to either the total diet of the animal, or to the body weight of the animals being fed.

It is believed that some beneficial effects on the immune system can be obtained with as little as 0.05 to 0.2 milligrams (mg) of HMB (Ca-HMB basis) per kilogram (kg) body weight per 24 hours. It will usually be desirable, however, to administer at least 0.5 mg/kg body weight/24 hrs (Ca-HMB basis). It will not usually be necessary to administer more than 100 mg HMB (Ca-HMB basis) per kilogram of body weight per 24 hours, but higher amounts can be given up to 400 to 500 milligrams HMB on the stated basis. An optimum range for most domestic animals is believed to be from about 15 to 35 mg/kg body weight/24 hrs (Ca-HMB basis).

As previously indicated, it is preferred to combine HMB with a complete feed ration, feed concentrate, or other dry feed material being given to the cattle, sheep, swine, chickens, or turkeys. In certain cases, however, HMB could be administered by dissolving it in drinking water for the animals. However, control of the amount administered in water can be expected to be more difficult. For more precise control, HMB could be orally administered in the form of pellets. For example, such pellets could be spread as a top dressing on the daily (24 hr) feed ration for each animal. Other methods of administration could be used.

As far as is known, HMB is not subject to significant rumen destruction. Following oral administration, the HMB salt appears to pass intact through the rumen into the intestines of the ruminant where it is absorbed. For the purpose of the present invention, it is believed that HMB should be absorbed into and distributed in the circulatory system.

The method of this invention can be used with cattle, including both beef cattle and dairy cattle, and with sheep, including both lambs and mature sheep, and swine, including both pigs and mature swine, and chickens, including both chicks and mature egg laying chickens, and also with turkeys being raised for meat production, as well as other domestic animals such as horses, dogs, and cats. The method can be used to offset stress-related conditions of domestic animals, such as cattle shipping fever, a bovine respiratory disease complex associated with the shipment of cattle. For five to ten days prior to shipment, the cattle can be fed the HMB. Alternatively or additionally, oral administration of HMB for counteracting shipping fever, the HMB may be parenterally administered, such as by intramuscular injection.

With respect to domestic animals subject to stress, it is believed that a further benefit of the HMB administration is to counteract increased cortisol. In most cases, it is believed that the improvement in T lymphocyte production will be accompanied by a reduction in the blood cortisol level.

USE OF HMB AS A HUMAN IMMUNOMODULATOR

Purified HMB, either in free acid or in the form of an edible salt, can be used as a human immunostimulator. Either oral or parenteral administration can be used. For example, HMB may be administered orally in the form of tablets or capsules, or it may be administered dissolved in an intravenous parenteral solution. For parenteral administration, the sodium salt of HMB (Na-HMB) is preferred.

Dose levels for a human subject can range from 200 to 3,000 milligrams (mg) per 24 hours. This administration can be repeated on a daily basis until the desired effect on the immune system is obtained. A preferred administration range is from 500 to 2,500 mg/24 hrs. Based on the presently available experimental information from animals models, it is believed that an optimum human dosage is from about 1 to 2 grams (gms) per day per 24 hrs. The dose level should be adequate so as to enhance the blastogenesis function of T lymphocytes. This is a function which can be monitored, and the dose required for the particular human subject can be regulated to obtain and maintain enhanced blastogenesis.

HMB salts, such as particularly the calcium salt, can be tabletted in uniform dose amounts. If needed a tabletting composition such as dextrose or sucrose can be admixed with the HMB salt for forming into tablets. Alternatively, dose amounts of the HMB salt may be incorporated in capsules. For example, each tablet or capsule may be prepared to contain one gram or two grams of HMB on a Ca-HMB basis.

The method of this invention is further illustrated by the following experimental examples.

EXAMPLE 1

Preparation of Ca-HMB

Reaction is contained in a 5000 ml round bottom flask fitted with condenser. Constant mixing is achieved by a magnetic stirrer.

Add in sequence:
1 gallon bleach (5.25% Sodium Hypochlorite)

45g NaOH powder
Mix well.
150 ml 1,4 Dioxane
93ml 4-Hydroxy-4-Methyl-2-Pentanone.
Reflux for 40 minutes.
Transfer solution to washtub and cool for 30 minutes under a hood.
Adjust pH to 5 using concentrated $H_2SO_4$. (HMB is stabilized.)
Transfer solution to cooling pans under a vent hood, so that air is drawn in over the solution for faster evaporation. Use the steam table if possible.
Let solution evaporate overnight. Sodium sulfate salts will precipitate out forming a slurry.
Transfer slurry to washtub, and adjust pH to 1 using concentrated $H_2SO_4$.
Salts and solution may be extracted separately depending on the volume available after evaporation.
Transfer solution with/without salts to 10 liter bottle, and wash 4x with approximately 2 liters of Ethyl Acetate (Acetate layer contains HMB.)
Save ethyl acetate layer. Discard final acid layer.
Roto Vap Acetate layer at 50° C.
Salts may precipitate out.
Solubilize Ultra-pure $H_2O$.
Add an equal volume of Ethyl Acetate and re-extract. Save ethyl acetate layer.
Roto Vap Acetate layer at 50° C.
Increase Temperature to 70° C. and continue Roto Vap. Remaining solution contains HMB and is ready for crystallization.

The dried HMB acid is neutralized with calcium hydroxide powder. The powder is added to the stirring HMB acid until a basic pH is reached. The pH is assessed with pH paper. The HMB solidifies at this point and is subsequently dissolved in hot 95% ethanol at a volume of ~10 times the original acid volume. Material that does no dissolve is removed from the liquid by centrifugation or filtration. The ethanol-HMB solution is then placed at $-20\%F$ until the mixture crystallizes. Usually this takes overnight but ca take 2-3 days. The HMB crystals are then filtered under vacuum through paper towels and liquid squeezed out of the cake-like crystals. The HMB crystals are then redissolved in hot ethanol and the process repeated. In most cases 3 recrystallizations are sufficient to fully remove any yellow color from the crystals. Further purification can be achieved by further crystallization. After the final crystallization the HMB is placed in a pan and freeze-dried overnight to obtain an anhydrous calcium HMB powder ready for feed additive use.

EXAMPLE 2

Stability of HMB in the Rumen

Rumen fluid was collected from a fistulated steer. After filtration and dilution (1:4) with an artificial saliva, 25ml of the solution was added to 50ml plastic tubes. Each tube was fitted with a one-way valve to allow gases to escape while not allowing air into the tube. Each tube was then gassed with C02 and incubated at 39° C. After 30 min a solution of KIC or HMB was added to the tube in concentrations to simulate what would be present in the rumen of an animal consuming .05% of the diet as KIC or HMB. It was estimated that a 50uM concentration would be attained in this case. At timed intervals 50ul samples of this rumen fluid were taken and analyzed for KIC and HMB. The results are shown in Table A.

TABLE A

| Time after Addition (min) | KIC | HMB |
|---|---|---|
| 0 | 30* | 60 |
| 15 | 15 | 76 |
| 30 | 4 | 81 |
| 60 | 2 | 71 |
| 240 | 2 | 74 |
| 480 | 1 | 74 |

*Initial concentration of KIC was estimated. The initial concentrations should have been ~50 uM but because of the rapid degradation of KIC in the rumen, KIC was already being degraded before the 0 time collection could be cooled and processed.

The foregoing shows that KIC is rapidly destroyed by the rumen bacteria while HMB is quite stable in a rumen environment.

EXAMPLE 3

In Vitro Effects of HMB on Cultured LYmphocytes

Materials and Methods

Lymphocyte Blastogenesis Determinations. Blood collections, lymphocyte isolation and blastogenesis assays were performed on isolated bovine cells by using a 3-d culture procedure as described previously in Kuhlman, et al. (1988), *J. Nutr.*, 118:1564–1569.

Isolated lymphocytes were exposed to 1 and 10 mM Leu and KIC and the metabolites isovalarate, $\beta$-hydroxy-$\beta$-methyl butyrate (HMB), $\beta$-hydroxy-$\beta$-methyl glutarate, butyrate, acetate, acetone, acetoacetate, and $\beta$-hydroxy butyrate (BOHB). The cells were then stimulated with the mitogen phytohemagglutinin, and incorporation of $^3H$-thymidine into the DNA of the dividing lymphocytes was measured.

Leucine and Leucine Metabolites. Most of the compounds listed in Table B were purchased from Sigma Chemical Company, St. Louis, MO. KIC was purchased from SOBAC (Paris, France), HMB was synthesized as described in Example 1, and the calcium salt of HMB was purified by crystallization in 95% ethanol. The calcium salt was converted to a sodium salt form and used in subsequent assays. The pH of all compounds was adjusted to approximately 7.3. Compounds were passed through a 0.2-um filter assembly to assure sterility.

The results of this study are summarized in Table B.

TABLE B

Effect of Leucine or Leucine Metabolites on In Vitro Lymphocyte Blastogenesis Compared with No Additions (Mean Percent Change~SEM)

| Metabolite Added | Final Concentration | % Change from No Additive | P< |
|---|---|---|---|
| Leucine | 1 mM | −12 ± 6 | 0.10 |
| α-ketoisocaproate | 1 mM | −3 ± 7 | |
| β-hydroxy-β-methyl glutarate | 1 mM | +28 ± 9 | 0.10 |
| β-hydroxybutyrate | 1 mM | +25 ± 6 | 0.05 |
| β-hydroxy-β- methyl butyrate | 1 mM | +78 ± 13 | 0.01 |

The data of Table B shows that leucine (Leu) tended to suppress blastogenesis while α-ketoisocaproate (KIC) had no effects on blastogenesis. β-hydroxy-β-methyl glutarate and β-hydroxybutyrate increased blastogenesis slightly while β-hydroxy-β-methyl butyrate (HMB) was 3 times more potent than any other compound at 1 mM concentrations. This study indicates that KIC and Leu have no effect on he immune system directly, but that only by partial conversion to HMB they positively effected lymphocyte function.

EXAMPLE 4

HMB Effects on Lymphocyte Function in Lambs

Materials and Methods

Animals and Experimental Design. Three sets of twin lambs were housed individually in fiberglass pens. Animals were randomly assigned to control or HMB diets, using a standard basal diet with and without 0.05% HMB.

Blood Sampling and Lymphocyte Preparation. In the first experiment, animals were bled for lymphocyte blastogenesis assays and T-cell subset analysis 38, 45, and 52 days after dietary treatments began. Blood (50 ml) was collected, aseptically, via jugular venepuncture into 10 ml acid-citrate-dextrose anticoagulant (44 g trisodium citrate, 16 g citric acid and 50 g dextrose per 1 of triple-distilled water). Blood was centrifuged, the buffy coat removed, and 1 volume of buffy coat was diluted with 0.5 volume of plasma which was added to 2 volumes of Sepracell-MN (Sepratech Corporation, Oklahoma City, Okla.). After further centrifugation at 1500 x g for 25 min, the mononuclear layer was removed and washed twice with Hanks' balanced salt solution (HBSS; Gibco, Grand Island, N.Y.) by centrifuging at 150 x g for 15 min. The remaining white blood cells were resuspended in HBSS, and the total number of white blood cells was determined by using an automated cell counter (Coulter Electronics, Hialeah, Fla.). The concentration of the cells was adjusted to $1 \times 20^{6''}$ cells/ml with HBSS.

Lymphocyte Blastogenesis Determinations. Blastogenesis assays were performed on isolated lymphocytes by using a 3-d culture procedure as described previously. Briefly, isolated lymphocytes were cultured in microtiter plates with $2 \times 10^{5''}$ cells in 0.15 ml of culture medium/well. Culture medium consisted of RPMI media-1640 (Gibco, Grand Island, N.Y.) containing 15% heat-inactivated fetal bovine serum and 1% antibiotic-antimycotic solution (Gibco, Grand Island, N.Y.). Unstimulated and mitogen-stimulated cultures were assayed in triplicate. Mitogens used were phytohemagglutinin-P (PHA), concanavalin A (ConA) and pokeweed mitogen (PWM). PHA was purchased from Difco Laboratories, Detroit, MI; ConA from Miles Laboratories, Elkhart, IN; and PWM from Gibco, New York, N.Y. Microtiter plates were incubated at 37° C. in a humidified 5% $CO_2$ atmosphere. After 48 h, 0.25 uCi of $^3$H-thymidine (New England Nuclear, Boston, Mass.) was added to each well. Eighteen hours later, the cultures were harvested onto glass-fiber filters with an automated sample harvester (Flow Laboratories, Rockville, Mo.), filters were placed in 10 ml CytoScint scintillation solution (ICN Biomedicals, Irvine, CA), and radioactivity was counted in a liquid scintillation counter. This procedure is similar to that described by Kuhlman, et al., J. Nutr., 118:1564-1569.

The results of the study of lymphocyte immune function are summarized in Table C.

TABLE C

| | Decays Per Min of 3H Thymidine Incorporated into Isolated Lymphocytes | | |
|---|---|---|---|
| | PHA Stimulation | ConA Stimulation | PWM Stimulation |
| Before Treatment | | | |
| Control | 37,000 | 48,000 | 32,000 |
| HMB | 23,000 | 41,000 | 21,000 |
| After Treatment | | | |
| Control | 15,000 | 19,000 | 18,000 |
| HMB | 18,000 | 21,000 | 25,000 |
| Change in control | −22,000 | −29,000 | −14,000 |
| Change in HMB | −5,000 | −20,000 | +4,000 |

The data of Table C indicates that HMB tended to effect the decline in lymphocyte function that occurred in these sheep. Why lymphocyte function in these animals decreased with time is not known. It may have been due to age, stress, or other unknown events. There is no reason to associate the decline with the HMB administration since it occurred to a greater extent in the control animals.

EXAMPLE 5

Stimulation of Pig Immune Function

Materials and Methods

Twelve specific pathogen free (SPF) pigs 4–5 weeks of age were distributed into two groups, each being blocked by gender and litter. All pigs were fed approximately 4% of their body weight of a commercially purchased starter ration. Pigs were penned individually and allowed free access to water.

Diets were supplemented with one of two dietary treatments: Control (limestone)(n=6) and HMB (n=6). Dietary treatments were fed at 0.05% of the body weight. HMB was synthesized by the method of Example 1. One week later, pigs were injected with 5 ml/30 kg body weight of a 20% suspension of sheep red blood cells (SRBC) subcutaneously.

Fourteen days post dietary treatments, all pigs were challenged via intratracheal inoculation with 5 ml of a ground lung suspension. The suspension was derived from pig pneumonic tissue obtained from a pig experimentally inoculated with Mycoplasma hyopneumoniae. Blood samples were collected once a week for the evaluation of antibodies produced in response to the SRBC and Mycoplasma hyopneumoniae antigenic stimuli. An agglutination assay was used to determine antibody titers produced against SRBC. Titers to Mycoplasma hyopneumoniae were determined using a serum complement fixation assay. At necropsy, the extent of macroscopic pneumonia lesions was recorded and samples from all pigs were submitted for histopathology to assay microscopic lesions. Lung and bronchi samples were cultured and evaluated for the presence of Mycoplasma species (i.e., M. hyorhinis, M. hyosynoviae, and M. hyopneumoniae) and other easily isolated bacteria (i.e., bordetella, pasteurella, and hemophilus).

The iliac lymph nodes, liver, spleen, and gastrocnemius muscle were removed from the carcass and weighed. The nasal cavity was examined for evidence of Bordetella broncheseptica infection that will result in nasal turbinate degeneration. Nasal degeneration was scored as to severity with 0 indicating no lesions and the highest score, 3, corresponding to moderate degeneration.

The results ar summarized below in Table D.

TABLE D

Effect of HMB Supplementation on
Disease Parameters in Pigs Infected with Mycoplasma

|  | Control | HMB |
|---|---|---|
| % lung showing lesions | 18.7 | 13.7 |
| Bronchi, presence of bacteria | 1.1 | 0.8 |
| Lung fluorescent antibodies to M. hyopneumoniae | 12.6 | 10.3 |
| M. hyopneumoniae peak titers | 7.1 | 6.7 |
| Red blood cell titers (dilution) day 10-15 | 11.6 | 15.5* |
| Nasal degeneration scores (0 = no lesion) | 1.6 | 0.8* |
| Spleen (g) | 101 | 94 |
| Iliac lymph node (g) | 3.8 | 3.3* |

*= p < .05

The results presented in Table D describe the macroscopic and microscopic lung evaluations and also the antibody values derived from M. hyopneumoniae stimuli. Although the fluorescent antibody technique showed the presence of M. hyopneumoniae colonies were decreased, when HMB was fed no significant differences were seen in the lung or bronchi evaluations. There were also no significant differences seen between dietary treatments when M. hyopneumoniae antibody titers were compared. Although not statistically significant, HMB fed animals had a lesser extent of mycoplasmal lung infection than did KIC-fed or control animals. HMB-fed animals demonstrated a significant decrease in nasal degeneration due to bordetella infection. The spleen and the iliac lymph node were smaller in HMB-fed animals.

In the comparison of control and HMB fed pigs infected with M. hyopneumoniae, the results suggested that HMB can prevent some of the lung damage associated with a Mycoplasmal lung agent. In particular, this agent is very difficult to treat with antibiotics because of the location within the bronchi of the lung. Therefore, stimulation of the animals' lymphocytes to enter and suppress o kill the Mycoplasmal organism is desirable. Evidence for this effect was the lower incidence of diseased lung and fewer numbers of Mycoplasma in the lung tissue. Also lower antibodies to the Mycoplasma in the plasma suggest less antigenic stimulation. Other opportunistic bacteria also appeared to be suppressed by HMB treatment as evidenced by fewer bacteria cultured in the bronchi and less severe lesions of the nasal turbinates caused by the bacteria Bordetella broncheseptica.

I claim:

1. The method of activating the immune function of T lymphocytes of mammals in need of such treatment, comprising administering to said mammals $\beta$-hydroxy-$\beta$-methyl butyric acid or an edible water-soluble salt thereof (HMB), said HMB being administered by a route in which the HMB enters the blood of the mammals and in an amount effective for enhancing the blastogenesis of their T lymphocytes.

2. The method of claim 1 in which said mammals are selected from the group of domestic animals consisting of cattle, sheep, and swine.

3. The method of claim 1 in which said mammals are humans.

4. The method of claim 2 in which the HMB is administered by admixing with feed for said mammals, and the HMB (Ca-HMB basis) is administered in an amount from 0.5 to 100 milligrams (mgs) per kilogram (kg) of body weight per 24 hours.

5. The method of claim 3 in which said HMB (Ca-HMB basis) is orally or parenterally administered in an amount of 500 to 2,500 milligrams (mg) per human subject per 24 hours.

* * * * *